US008524685B1

(12) United States Patent
Banerjee

(10) Patent No.: US 8,524,685 B1
(45) Date of Patent: Sep. 3, 2013

(54) ANTI-ANGIOGENIC THERAPEUTICS EFFICACY ENHANCED BY NANOFORMULATION

(75) Inventor: Dipak K Banerjee, Guaynabo, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 13/290,875

(22) Filed: Nov. 7, 2011

Related U.S. Application Data

(60) Provisional application No. 61/410,982, filed on Nov. 8, 2010.

(51) Int. Cl.
*A01N 43/04* (2006.01)
*A61K 31/70* (2006.01)

(52) U.S. Cl.
USPC .................. 514/50; 514/23; 514/25; 514/49; 514/62

(58) Field of Classification Search
None
See application file for complete search history.

(56) References Cited

U.S. PATENT DOCUMENTS 7,361,643 B2 * 4/2008 Banerjee et al. ................ 514/50

* cited by examiner

*Primary Examiner* — Patrick Lewis
(74) *Attorney, Agent, or Firm* — Hoglund & Pamias, PSC; Roberto J. Rios

(57) ABSTRACT

Preparation of nano-conjugated Tunicamycin enhances the efficacy of the drug Tunicamycin. The invention provides several nanoformulations such as Tunicamycin encapsulated in peptide nanotubes, nanotubes bound to gold nanoparticles conjugated with Tunicamycin, Tunicamycin conjugated with nanotubes, gold nanoparticles bound to tubes and conjugated with Tunicamycin, and gold nanoparticles conjugated with Tunicamycin.

3 Claims, 3 Drawing Sheets

ANTI-ANGIOGENIC THERAPEUTICS EFFICACY ENHANCED BY NANOFORMULATION

BACKGROUND OF THE INVENTION

Breast cancer is a multi-factorial disease and depends on the genetic make up, the metabolomic profile of the individual as well as on the environment. A great diversity in the breast cancer incidence rate suggests both endogenous and exogenous factors contribute to the development and progression of the disease. The etiology of breast cancer is complex, but this hyperproliferative disorder is angiogenesis dependent, is a critical process in which the dynamic balance between pro-angiogenic and anti-angiogenic factors is shifted to the former by conditions created by the tumor and its microenvironment, including hypoxia, inflammation, and mutation in oncogenes or tumor suppressor genes, such as p53. Commonly known pro-angiogenic factors are vascular endothelial growth factor (VEGF), basic fibroblast growth factor (bFGF), epidermal growth factor (EGF), platelet-derived growth factor (PDGF), placental growth factor (PlGF), and matrix metalloproteinases (MMPs). Endogenous anti-angiogenic factors include thrombospondin, angiostatin, tumstatin, and endostatin.

The prognosis of breast cancer depends upon the stage at which the tumor is diagnosed. The breast cancer statistics of 2010 estimated that the US will have 207,090 new cases of invasive and 54,010 new cases of non-invasive (in situ) breast cancer and about 39,840 will die from the disease. Although there are several therapeutic options, treatment is typically expensive and accompanied by a host of adverse side effects that are detrimental to patients' quality of life. In many cases, treatments are effective in only a small percentage of the total patient population so, multiple treatment options must be pursued sequentially until an effective option is found. The consequences of the suboptimal or in appropriate therapies include poor patient outcomes (both from side effects and lack of activity), as well as an economic burden on the healthcare system, the added costs of the physician's time, wasted drugs and increased hospitalization. Normal vasculature is quiescent in healthy adults with each endothelial cell dividing once every 10 years. In contrast, tissue remodeling and angiogenesis are crucial for the growth and metastasis of breast cancer, providing an attractive therapeutic target. Treatment strategies include either (a) targeting angiogenesis with endothelial toxins, growth factor antagonists, protease inhibitors, endogenous anti-angiogenics, anti-angiogenic chemotherapy, or (b) other targets.

Several lines of evidence now indicate that N-linked glycoproteins play an important role in capillary endothelial cell proliferation and differentiation. It has been suggested earlier that deoxymannojirimycin (an inhibitor of hybrid and complex-type N-glycans), inhibited the formation of capillary tubes when tested in vitro by plating capillary endothelial cells on fibronectin-coated dishes. In contrast, swainsonine (an inhibitor of complex-but not hybrid-type N-glycans), did not inhibit tube formation. Lectin affinity chromatography of 2-[$^3$H] mannose-labeled glycopeptides from endothelial cells induced to form tubes did not reveal a striking difference in the spectrum of glycans compared to uninduced cells. However, the glycopeptides from swainsonine-treated cells were enriched in monosialylated hybrid-type glycans sensitive to alpha-fucosidase, beta-galactosidase, and beta-N-acetylhexosaminidase, suggestive of sialyl Lewis-X determinants.

Tunicamycin (a glucosamine-containing pyrimidine nucleoside and an antibiotic), a competitive inhibitor of N-acetylglucosaminyl 1-phosphate transferase has recently been shown to inhibit angiogenesis in vitro/in vivo as well as the breast tumor microvasculature and reduce the breast tumor growth in athymic nude mice. Tunicamycin was effective in double and triple negative breast tumors. The effect is mediated by ER stress followed by developing the unfolded protein response (upr) in tumor microvasculature and the induction of apoptosis.

Gold nanoparticles (NPs) and peptide-based nanostructures have been receiving significant attention over the past decade due to their potential applications in catalysis, chemical sensing, electronics, optics, sensors and biomedical applications. Particularly, monolayer-protected Au NPs using thiolated compounds to stabilize Au NPs have been gaining popularity for delivering various therapeutic agents such as drugs, proteins, and nucleic acids into their targets. Several types of Au NP conjugates have been prepared for potential drug delivery applications. For example, recent report indicated that polystyrene-functionalized Au NPs by the covalent attachment of thiol-terminated polystyrene has been prepared by anionic polymerization. Synthesis of Au NPs with tetra (ethylene glycol)ylated cationic ligands, fluorogenic ligands as well as polycaprolactone-methoxy poly(ethylene glycol) have also been carried out for the development of drug delivery systems. In a separate study, NP-polymer transfection vectors have recently been synthesized as well. While gold nanoparticles provide a versatile platform for the preparation of drug delivery devices, peptide based nanotubes self-assembled from peptide bolaamphiphiles (amino acid head groups covalently bound via hydrocarbon chain), exhibit several properties that make them promising biomaterial candidates, including facile self-assembly in aqueous solutions and adaptability to functionalization for increased biocompatibility. Further, the peptide head groups can be readily modified in order to manipulate and potentially alter the properties of the self-assembled micro and nanostructures. Although many applications related to peptide-based nanotubes have been investigated, the immense potential of peptide nanotubes as drug delivery devices is yet to be fully tapped.

SUMMARY OF THE INVENTION

The present invention has conjugated the anti-angiogenic drug, Tunicamycin with gold nanoparticles. Furthermore, the drug has also been encapsulated in peptide nanotubes containing threonine moieties as an alternative drug delivery device for breast cancer therapy.

Preparation of nano-conjugated Tunicamycin enhances the efficacy of the drug, due to the high surface to volume ratio of the nanomaterials. Decreased viability of capillary endothelial cells by these nano-configurations was confirmed by the MTT assay. Induction of ER stress as well as the development of unfolded protein response-mediated signaling by these nanoconjugated-Tunicamyin was confirmed by the up-regulation of GRP-78/Bip expression, and down-regulated expression of IRE-1 and phosphoPERK. Inhibition of DPMS expression by westernblotting also supported cross-talk between multiple enzymes.

BRIEF DESCRIPTION OF THE DRAWINGS

Further features and advantages of the invention will become apparent from the following detailed description taken in conjunction with the accompanying figures showing illustrative embodiments of the invention, in which.

Figure 1:
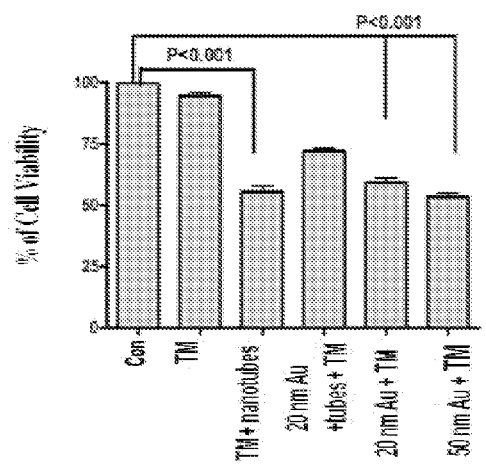
FIG. 1 shows a plot of the percentage of cell viability according to an embodiment of the invention.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

Materials and Methods
  Materials—
  Hydroxyurea, dimethylsulfoxide, nystatin, anti-phosphoserine monoclonal antibody, ethylenediamine tetra acetic acid (sodium salt) and Tunicamycin were obtained from Sigma Aldrich (St. Louis, Mo.). Rabbit polyclonal antibody for GRP-78 was from Santa Cruz Biotechnology (Santa Cruz, Calif.). HRP-conjugated goat anti-rabbit IgG/anti-mouse IgG, streptavidin and ECL chemiluminescence detection kit were from GE Healthcare (Piscataway, N.J.). TRIzol was from Invitrogen Life Technologies (Carlsbad, Calif.). PCR grade water and DNA decontamination kit were from Applied Biosystems (Ambion Inc; Austin, Tex.), iScript c-DNA synthesis kit, biotinylated protein molecular weight markers, DNA markers and all electrophoresis reagents were obtained from Bio-Rad Laboratories (Hercules, Calif.). All other chemicals and solvents used were of the highest purity available. All cell culture wares were from Sarstedt (Newton, N.C.) and fetal bovine serum was purchased from HyClone Laboratories (Logan, Utah). The nanoparticles of various sizes were either synthesized in the laboratory or purchased from Electron Microscopy Sciences.

Synthesis and Self-Assembly of Nanotubes:
  The bolaamphiphile bis(N-α-amido-threonine)1,3-propane dicarboxylate contains threonine head groups, which are connected by a propyl carbon chain and was synthesized according to previously established methods. The intermediate obtained was washed with cold citric acid and sodium bicarbonate and recrystallized from dimethyl formamide (DMF). The product obtained was washed with cold acetone, and recrystallized from methanol. Individual stock solutions (8 mM) of the bis(N-alpha-amido-threonine)-1,3 propane dicarboxylate monomers were prepared in buffer solution of pH 5. In general, the materials were allowed to self-assemble for 7-10 days. Aggregates of nanotubular assemblies formed were then washed in nanopure water, followed by sonication for 30 min. The formed nanotubes were then used for binding to Tunicamycin either by adsorption or by covalent binding between the carboxyl groups of the nanotubes and the —OH groups of tunicamycin. The attachment of Tunicamycin to the microtubes was confirmed by Fourier transformation infrared spectroscopy, transmission electron microscopy, and absorbance spectroscopy.

Attachment of Tunicamycin to the Self-Assembled Nanotubes:
  The self-assembled nanotubes possess free carboxylic groups, which can be chemically modified. For binding the tunicamycin to the nanotubes, we conducted a selective esterification reaction between the primary alcohol group of tunicamycin and the carboxylic acid groups of the nanotubes. Selective esterification of primary alcohols in the presence of secondary alcohols requires the use of specific catalytic agents. It has been shown that the use of catalysts such as $Hf(IV)_4$ or $Zr(IV)_4$ salts or 2,4,6-Trimethylpyridine have been efficient in selective esterification of primary alcohols, primarily due to the difference in the reacitivities of the primary and secondary alcohol groups. Tunicamycin possesses a single primary alcohol group and seven secondary alcohol groups. In order to selectively bind the primary alcohol group of Tunicamycin to the nanotubes, without causing any major change to the other functional groups first, the nanotubes were dried at 50° C. overnight under nitrogen in order to remove any residual water. Next, the dried nanotubes were treated with thionyl chloride in the presence of triethylamine to convert the carboxyl acid groups to the corresponding acid chlorides. The product obtained was centrifuged. The nanotubes were then allowed to react with the Tunicamycin (1.0 mmol) in the presence of 2,4,6-Trimethylpyridine (1.5 eq) in DMSO for 2 hours at 20° C. The formed products were then centrifuged several times and washed thoroughly with nanopure water to remove any reacted excess reagents. The formation of the esterified product was confirmed by FTIR spectroscopy of the functionalized nanotubes.

Encapsulation of Tuncamycin within Threonine Based Peptide Nanotubes:
  The incorporation of Tunicamycin into the nanotubes was examined by incubating the drug with the nanotubes. Since, the threonine nanotubes possess free hydroxyl groups and carborxylic acid groups, it was hypothesized that it would be able to interact with Tunicamycin via strong hydrogen bonding interactions. Tunicamycin was encapsulated into the nanotubes by incubating the drug with the nanotubes at 4° C. for 48 hours under mild agitation. The samples were then washed and centrifuged in order to remove the excess Tunicamycin not incorporated within the nanotubes. The incorporation of Tunicamycin was confirmed by TEM and FTIR analyses.

Conjugation of Gold Nanoparticles to Tunicamycin:
  The gold nanoparticles (20 nm or 50 nm) were incubated with reduced lipoic acid, thus functionalizing the nanoparticles with the thiol groups, while the carboxylic groups would be free to react. The nanoparticles of various sizes were either synthesized in the laboratory or purchased from Electron Microscopy Sciences. The nanoparticles were allowed to react with reduced lipoic acid in nanopure water for 24 hours at 4° C. under mild agitation under nitrogen. The nanoparticles were then washed and centrifuged to remove any unbound lipoic acid. The incorporation of the lipoic acid was confirmed by the shift in the absorbance spectrum observed for the nanoparticles. The functionalized nanoparticles were then treated with Tunicamycin in the presence of 2,4,6-Trimethylpyridine (1.5 eq) in DMSO for 3 hours at 20° C., washed, centrifuged, and dialyzed using snake skin dialysis tubing to remove any unreacted products. The incorporation of Tunicamycin to the nanoparticles was confirmed by transmission electron microscopy.

Culturing of Capillary Endothelial Cells—
  The capillary endothelial cells were from the laboratory stock of a non-transformed endothelial cell line from bovine adrenal medulla and maintained as previously described. Synchronized cultures (33) were treated with Tunicamycin nanoparticles (1 μg/ml) for 1 h in EMEM containing 2% fetal bovine serum (heat inactivated).

SDS-PAGE and Western Blot Analyses—
  Performed as before with 7.5% gel concentration.

Results

Effect of Tunicamycin Nanoparticles on Cell Viability:

Synchronized capillary endothelial cells were incubated with Tunicamycin (1 μg/ml) alone or with 1 μg/ml of Tunicamycin nanoparticles for 3 h at 37° C. in a $CO_2$ incubator (5% $CO_2$ and 95% air) in 96-well microtiter plates. At the end the plates were processed for the MTT Assay. The results shown in FIG. 1 indicate that the cell viability was reduced to almost 50% ($p<0.001$) when treated with Tunicamycin conjugated to 20 nm or 50 nm gold particles. Native Tunicamycin at 1 μg/ml does not show any effect on the capillary endothelial cell viability compared to the control under a similar experimental condition. The logical conclusion would be that Tunicamycin gold nanoparticles are much more effective in killing capillary endothelial cells over that of the native Tunicamycin.

Figure 2:
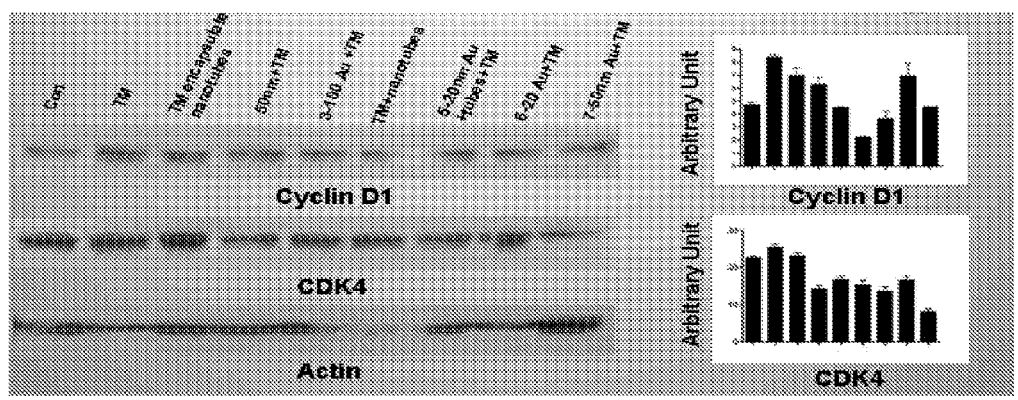
FIG. 2 shows comparative western blot plots, according to an embodiment of the invention.
Figure 3:
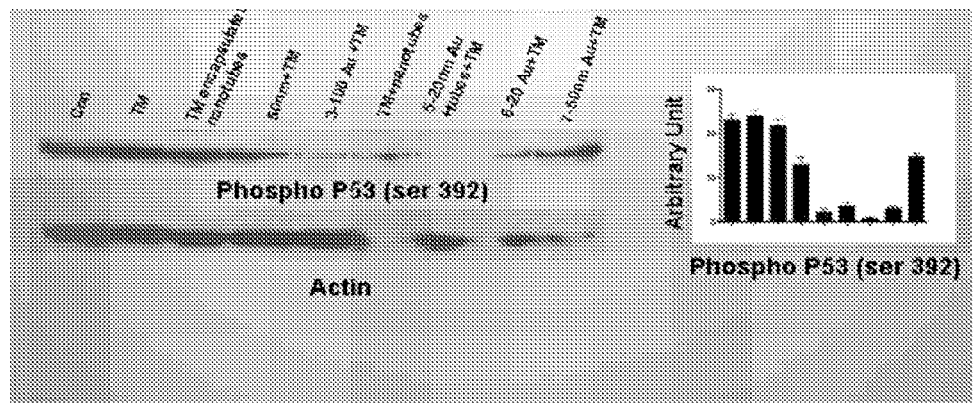
FIG. 3 shows western blot plots, according to an embodiment of the invention.

Tunicamycin Nanoparticles Inhibits Cell Cycle Progression:

To evaluate the biochemical pathway the Tunicamycin nanoparticles are likely to interfere, their effect on the cell cycle progression has been analyzed. The cell cycle antigens have been analyzed focusing primarily on the D-type cycline and their partners because Tunicamycin causes cell cycle arrest in G1. Expression of cycline and their partners because Tunicamycin causes cell cycle arrest in G1. Expression of cyclin D1 and its catalytic partner, i.e., CDK4 was analyzed by western blotting. Interestingly, the expression of both cyclin D1 and the CDK4 was enhanced in cells treated with native Tunicamycin compared to the untreated control. On the other hand, the expression of cyclin D1 was significantly reduced in cells treated with Tunicaycin conjugated either with 20 nm or 50 nm gold particles compared to the cells treated with native Tunicamycin but its expression remained unchanged when compared with the untreated control. There was a little difference with the CDK4 expression. It was higher in cells treated with 20 nm gold particles over the nm gold particles, but they both were much reduced compared to the untreated control or cells treated with native Tunicamycin as shown in FIG. 2. p53 is a gate keeper for the cell cycle. Upon phosphorylation p53 migrates to the nucleus and activates gene transcription. When analyzed, the expression of p53 phosphorylated in serine392 ($p53p^{ser392}$) in Tunicamycin gold-conjugated nanoparticles it was observed substantial reduction of $p53p^{ser392}$ expression in cells treated with 20 nm gold-conjugated Tunicamycin nanoparticles but it was comparatively less in cells treated with 50 nm nanoparticles. Native Tunicamycin at a similar concentration had no effect as shown in FIG. 3. It was therefore concluded that gold-conjugated Tunicamycin nanoparticles are much more effective in inhibiting the cell cycle progression than the native drug.

Figure 4:
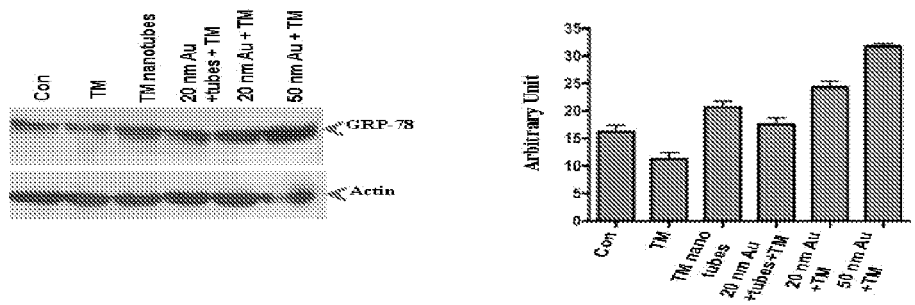
FIG. 4 shows western blot and comparative plots according to an embodiment of the invention.

Tunicamycin Gold Nanoparticles Induces ER Stress Much Faster:

It has been shown earlier that native Tunicamycin induces ER stress as early as 3 h of treatment. We then compared the development of ER stress in a synchronized population of capillary endothelial cells treated with Tunicamycin conjugated to 20 nm or 50 nm gold particles with that of native Tunicamycin. The ER chaperone, GRP-78/Bip was used as a marker. The results shown in FIG. 4 indicate that Tunicamycin gold nanoparticles of both sizes induced very high expression of GRP-78/Bip when compared with that of the untreated control or treated with native Tunicamycin. The conclusion is that Tunicamycin nanoparticles are much effective than the drug in its native formulation.

Figure 5:
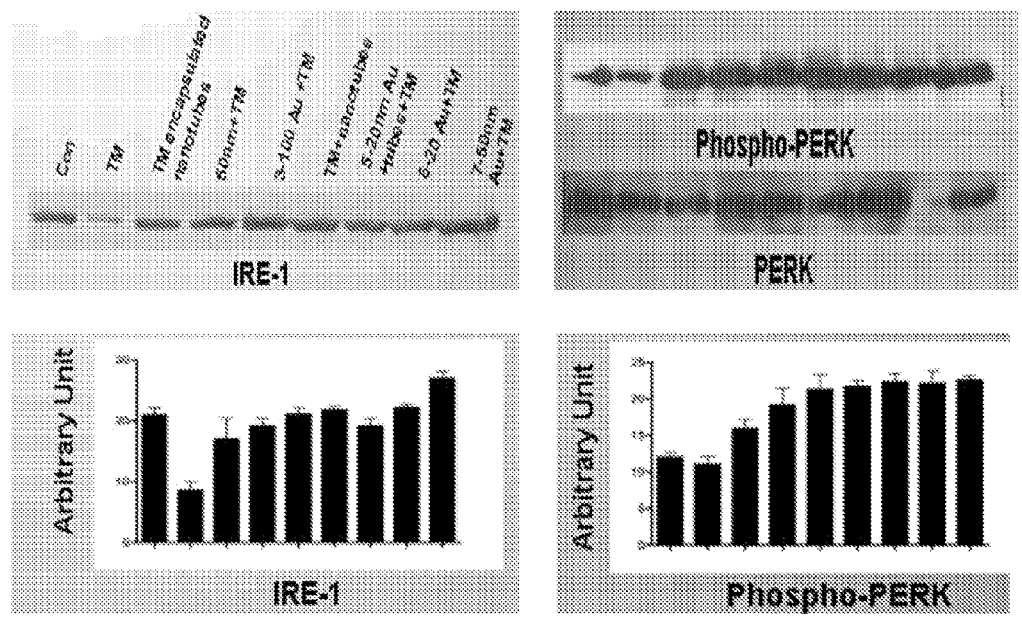
FIG. 5 shows western blot and comparative plots according to an embodiment of the invention.

Tunicamycin Gold Nanoparticles Induces Unfolded Protein Response-Mediated Apoptotic Death:

It has been observed recently that Tunicamycin inhibits angiogenesis in vitro and in vivo as well as during the breast tumor progression by ER stress-mediated induction of unfolded protein response. In addition, it has also been shown that Tunicamycin gold nanoparticles inhibit capillary endothelial cell cycle progression much more effectively than native Tunicamycin. It was also evaluated if Tunicamycin gold nanoparticles would also activate the pathway that induces the unfolded protein response. The results shown in FIG. 5 indicate that Tunicamycin gold nanoparticles affect both transcription and translation. For example, 50 nm gold nanoparticles of Tunicamycin activates IRE-1 (a transcriptional attenuator) but 20 nm gold particles have only the marginal effect. On the other hand, PERK and phosphoPERK (a translational attenuator) are activated significantly by both 20 nm and 50 nm Tunicamycin gold nanoparticles. Under a similar experimental condition, native Tunicamycin either had no effect or the effect is drastically reduced.

Figure 6:
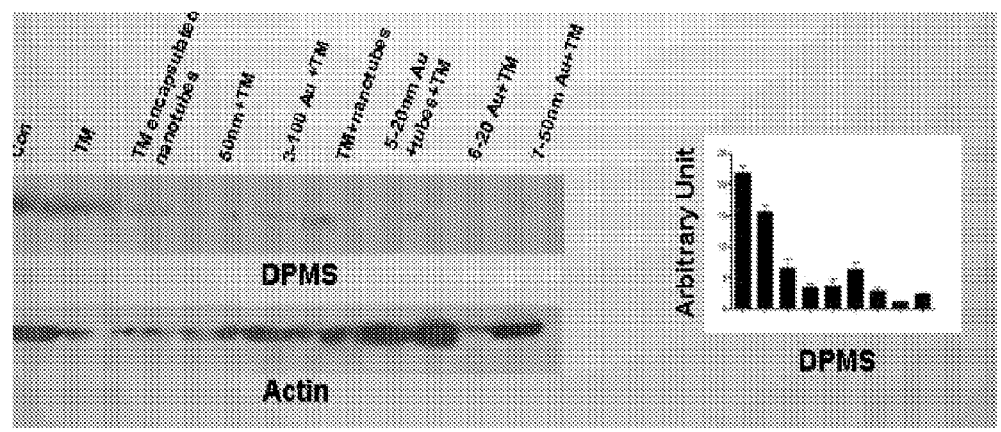
FIG. 6 shows comparative western blot plots, according to an embodiment of the invention.

Tunicamycin Gold Nanoparticles Down-Regulates DPMS Expression:

Mannosylphospho dolichol synthase (DPMS) is an obligatory requirement for the synthesis of lipid-linked oligosaccharide (i.e., $Glc_3Man_9GlcNAc_2$-PP-Dol) biosynthesis, a pre-requisite for N-glycosylation. It has been shown recently, that either phosphorylation upregulation of DPMS or a cell clone over expressing DPMS enhanced capillary endothelial cells and accelerated healing of the wound induced by a mechanical stress supported unequivocally the role of DPMS in angiogenesis. To evaluate the status of DPMS in cells treated with Tunicamycin gold nanaoparticles, the DPMS expression was analyzed by western blotting. The results shown in FIG. 6 convincingly supported that the expression of DPMS was reduced significantly in cells treated with Tunicamycin gold nanoparticles.

Although the present invention has been described with reference to the foregoing exemplary embodiment, this embodiment does not serve to limit the scope of the present invention. Accordingly, those skilled in the art to which the present invention pertains will appreciate that various modifications are possible, without departing from the technical spirit of the present invention.

I claim:

1. An enhanced anti-angiogenic drug comprising:
   Tunicamycin conjugated with a nano-structure material.
2. A method of preparing an enhanced anti-angiogenic drug comprising:
   conjugating Tunicamycin with a nano-structure material.
3. A method of inhibiting angiogenesis in a cell comprising:
   exposing said cell to a formulation of Tunicamycin conjugated with a nano-structure material.

* * * * *